United States Patent [19]
Arnett

[11] Patent Number: 5,848,125
[45] Date of Patent: Dec. 8, 1998

[54] RADIOPAQUE LANDMARK SKIN MARKERS AND METHOD

[75] Inventor: G. William Arnett, Santa Barbara, Calif.

[73] Assignee: Arnett Facial Reconstruction Courses, Inc., Santa Barbara, Calif.

[21] Appl. No.: 943,541

[22] Filed: Oct. 3, 1997

[51] Int. Cl.$^6$ ............................................. H05G 1/28
[52] U.S. Cl. ................................... 378/162; 378/210
[58] Field of Search ............................. 378/162, 163

[56] References Cited

U.S. PATENT DOCUMENTS

| | | | |
|---|---|---|---|
| 4,759,045 | 7/1988 | Lasky | 378/162 |
| 5,149,965 | 9/1992 | Marks | 378/163 |
| 5,394,457 | 2/1995 | Leibinger et al. | 378/162 |

*Primary Examiner*—Craig E. Church
*Attorney, Agent, or Firm*—Daniel R. Kimbell

[57] ABSTRACT

Radiopaque marker and method for use in nuclear medicine imaging, (particularly with X-ray radiology) of soft tissue landmarks of a patient's body. The radiopaque marker includes a spherical ball of radiopaque material attached to an adhesive sheet which is positioned on a sheet of release film. Radiopaque markers are removed from the release film and applied to soft tissue landmarks on the patient. The patient's body, with the radiopaque markers, is then imaged, e.g. with X-ray radiology. The radiopaque markers leave circular shadows on the X-ray film, regardless of the contours of the portion of the body to which the radiopaque markers are applied, and can be used to accurately mark soft tissue landmarks.

12 Claims, 2 Drawing Sheets

RADIOPAQUE LANDMARK SKIN MARKERS AND METHOD

FIELD OF INVENTION

The invention relates generally to the field of medical devices and accessories, and more particularly to skin markers and their use in mapping soft tissue landmarks on a patient using radiological techniques.

BACKGROUND OF THE INVENTION

There are numerous devices presently available to aid the medical professional in imagining structures of the body, including traditional radiology using X-ray cameras and film to produce two dimensional photographic images and the more advanced three dimensional computerized axial tomography (CAT) which takes a plurality of tomograms. Additionally, there are other techniques such as magnetic resonance imagining (MRI), ultrasound, photon emission tomography (ET), and single photon emission computed tomography (SPECT). In addition, even newer methods are being developed including magnetic source imaging, infrared noninvasive scanning, electrical impedance tomography, and microwave scanning.

While the availability of some of the newer and more exotic nuclear medical techniques show promise, traditional radiology using X-ray cameras and film remains one of the most cost effective, prevalent, and powerful diagnostic tools available to the health care professional.

In traditional X-ray radiology, a film is placed behind a part of the body to be imaged, and the body is briefly exposed to X-rays. Hard structure, like bone, image clearly, but soft structures like skin, fat, and muscles do not image very well. For example, in imagining a patient's head in profile, the profile of the face and head and underlying bony structures show up, soft tissue landmarks not on the profile, such as the anterior-most projection of the check, the lowermost portion of the orbital rim, the alar base (junction of widest point of nostril with check) are not visible at all on X-ray films.

For this reasons, various markers have been developed to allow the imagining of cutaneous landmarks. For example, U.S. Pat. No. 4,860,106 to Williams et al. discloses an adhesive tape structure with a plurality of radiopaque vertical lines, with biopsy needle holes formed between the parallel vertical lines. This structure is said to be useful during CAT scans to aid in locating the appropriate position to insert a biopsy needle.

U.S. Pat. No. 4,506,676 to Duska discloses an adhesive tape with a single, dashed radiopaque line present along the length of the tape. When applied to the skin, the dashed line will provide a dashed reference marker line.

U.S. Pat. No. 5,232,452 to Russell et al. discloses an alternate marker system for radiography which includes an elongate base tape, a bendable, fabric covered wire containing a material that is radiopaque, and a continuous row of adhesive pads fixedly aligned along the wire. The adhesive pads and the carried radiopaque wire are manually removable from the base tape together with the wire for releasable adherence to a subject. When imaged, the wire will show up as a continuous line.

U.S. Pat. No. 5,193,106 to DeSena discloses radiopaque stickers with flat shapes formed thereon including a circle, the outline of a square, and the outline of a triangle.

U.S. Pat. No. 3,547,121 to Cherry discloses a grid of radiopaque material for application to a woman's abdomen, and is for use in imagining the position of the fetus in the womb.

U.S. Pat. No. 5,306,271 to Zinreich et al. discloses radiation therapy skin markers used to delineate a radiotherapy protal area on a patient's skin surface. A variety of flat, radiopaque shapes are shown, and are adhesively attachable to the skin.

U.S. Pat. No. 5,469,847 to Zinreich et al. discloses a multi-modality skin marker for use in a variety of nuclear medical techniques such as X-ray, computerized tomography, positron emission tomography, and nuclear magnetic resonance imagining, which is generally cylindrical shaped with a central bore for insertion of a needle.

Lastly, U.S. Pat. No. 5,368,030 to Zinreich et al. ('030) discloses a non-invasive multi-modality radiographic surface marker for use in a variety of nuclear medical techniques such as X-ray, computerized tomography, positron emission tomography, and nuclear magnetic resonance imagining, which is generally cylindrical shaped with a central bore for insertion of a needle. Zinreich et al. ('030) discloses that depending on the angle at which the device is scanned, the marker may show up as disk-shaped, or as two wide dashed lines. Zinreich et al. ('030) further notes that there is a commercial product which uses a small, dense metal bead attached to adhesive tape.

U.S. Pat. No. 4,985,019 to Michelson discloses an X-ray marker which comprises an adhesively applied disk-shaped marker with a central needle bore, having a grid of radiopaque lines on the disk portion, which grid clearly shows up on the X-ray film. Michelson notes that there are known nipple markers that have a BB-like center portion for placement on the nipple before the taking of an X-ray to localize the position of the nipple on X-ray film.

The above noted references disclose various styles of radiopaque markers including flat radiopaque lines and different flat shapes on an adhesive backing, and cylindrical structures with central needle holes. As noted above, with the exception of Zinreich et al. ('030) (which mentions, without elaboration, a small, dense metal bead attached to adhesive tape) and U.S. Pat. No. 4,985,019 to Michelson, (which notes the existence of a nipple marker that has a BB-like center portion for placement on the nipple before the taking of an X-ray to localize the position of the nipple on the X-ray), there is no disclosure of a perfectly spherical radiopaque marker on an adhesive backing for use in marking the position of soft tissues in X-rays images. By using a plurality of perfectly spherical radiopaque markers applied to desired landmarks, regardless of the angle at which the structure is imaged, perfectly circular indicia will appear on the X-ray film. This is because the shadow of a sphere is always circular. In certain techniques, such as in the mapping of the facial structure for purposes of reconstructive surgery, extremely precise measurements of distances and angles of various soft and hard tissue landmarks is essential. With the above-noted radiopaque markers, depending on the angle at which the image is taken, and the contour of the structure to which the marker is applied, the shape of the shadows of the radiopaque markers can greatly vary. This can cause serious errors to be introduced into distance and angle calculations.

Accordingly, there remains a need for radiopaque markers and method which can be used with nuclear medicine techniques, such as traditional X-ray radiology and which will consistently give accurate position marking, regardless of the angle at which the image is taken and the contours of the structure to which the markers are applied.

DETAILED DESCRIPTION OF THE PREFERRED EMBODIMENTS

Referring first to FIGS. 1–4, one embodiment of the radiopaque marker 10 of the invention is shown. In this embodiment of the device, a spherical ball of radiopaque material 12, such as iron, stainless steel, lead, barium sulfate (or any other suitable material), is provided. The diameter of the spherical ball of the radiopaque material 12 can be sized as desired and necessary, and can conveniently be sized from about one millimeter or smaller to about four millimeter (or even larger), with a size of about two millimeters beings ideal for most purposes.

Figure 1:
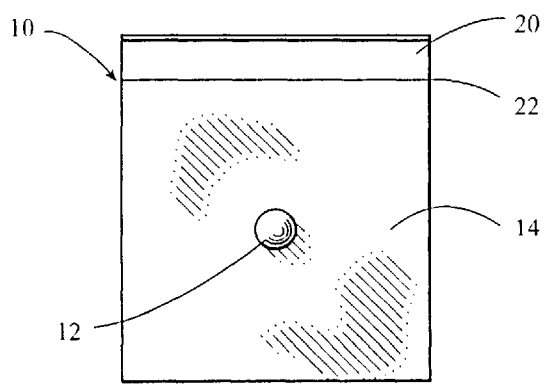
FIG. 1 is a plan view a one embodiment of the radiopaque marker of the invention.
Figure 2:
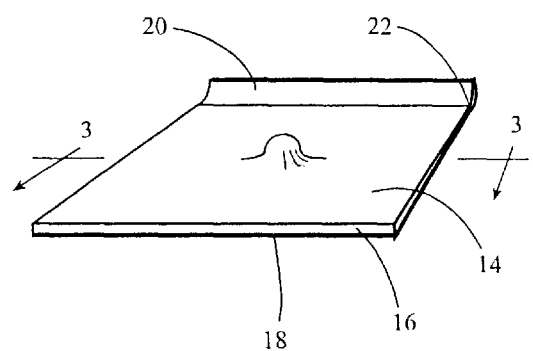
FIG. 2 is a perspective view of the radiopaque marker of FIG. 1.
Figure 3:
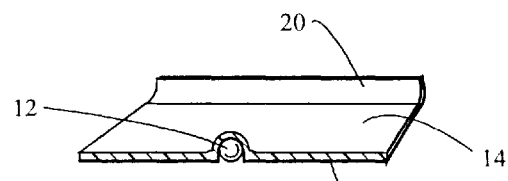
FIG. 3 is a cross-sectional view through view lines 3—3 of FIG. 2.
Figure 4:
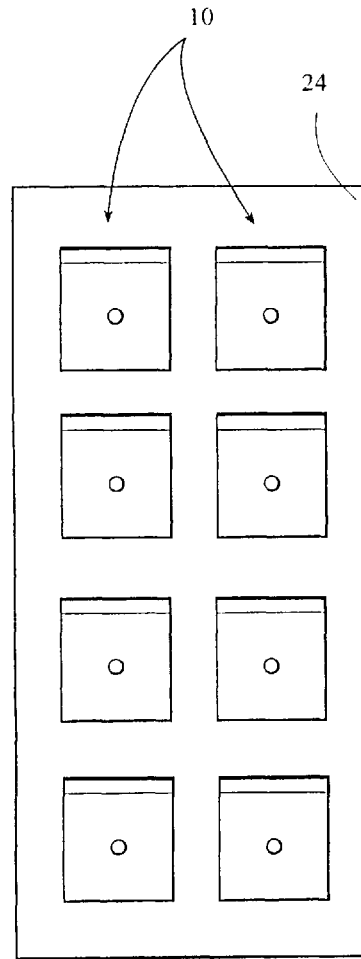
FIG. 4 is a plan view of a plurality of the radiopaque markers of FIG. 1 on a base sheet.

Spherical ball of radiopaque material 12 is affixed to a non-radiopaque portion 14, which can conveniently comprise a sheet of flexible material 16 with an adhesive film 18 on a lower surface thereof (like an adhesive strip.) A non-stick pull tab means or grip portion 20 is preferably provided to extend from an edge portion 22 of radiopaque marker 10 to permit easy grasping and removal of radiopaque marker 10 from a sheet of release film 24 and easy positioning on a patient's body. As shown in FIGS. 2 and 3, spherical ball of radiopaque material 12 can be adhered to adhesive film layer 18 on the underside of flexible sheet 16. Referring to FIG. 4, a plurality of radiopaque markers 10 can be provided on sheet of release film 24.

Figure 5:
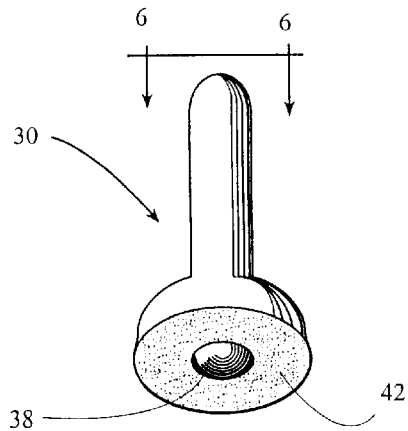
FIG. 5 is a bottom perspective view of another embodiment of the radiopaque marker of the invention.
Figure 6:
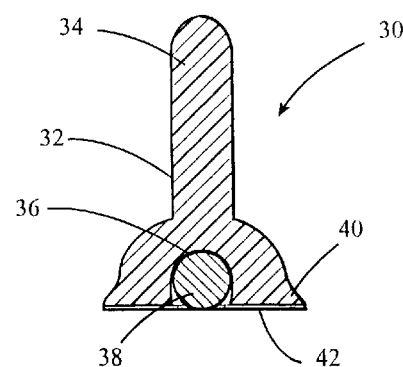
FIG. 6 is a cross-sectional view through view lines 6—6 of FIG. 5.

Turning to FIGS. 5 and 6, another embodiment of radiopaque marker 30 the invention is shown. In this embodiment, a non-radiopaque body portion 32 has a grip portion 34 and a hollow base portion 36 for receipt of a spherical ball of radiopaque material 38. A seating portion 40 is provided with adhesive means 42, such as a film or layer of adhesive. In radiopaque marker 30, an outermost portion of spherical ball of radiopaque material 38 extends downwardly to the level of the adhesive film 42, so that when radiopaque marker 30 is applied to the skin of a patient, spherical ball of radiopaque material 38 contacts the skin of the patient.

Figure 7:
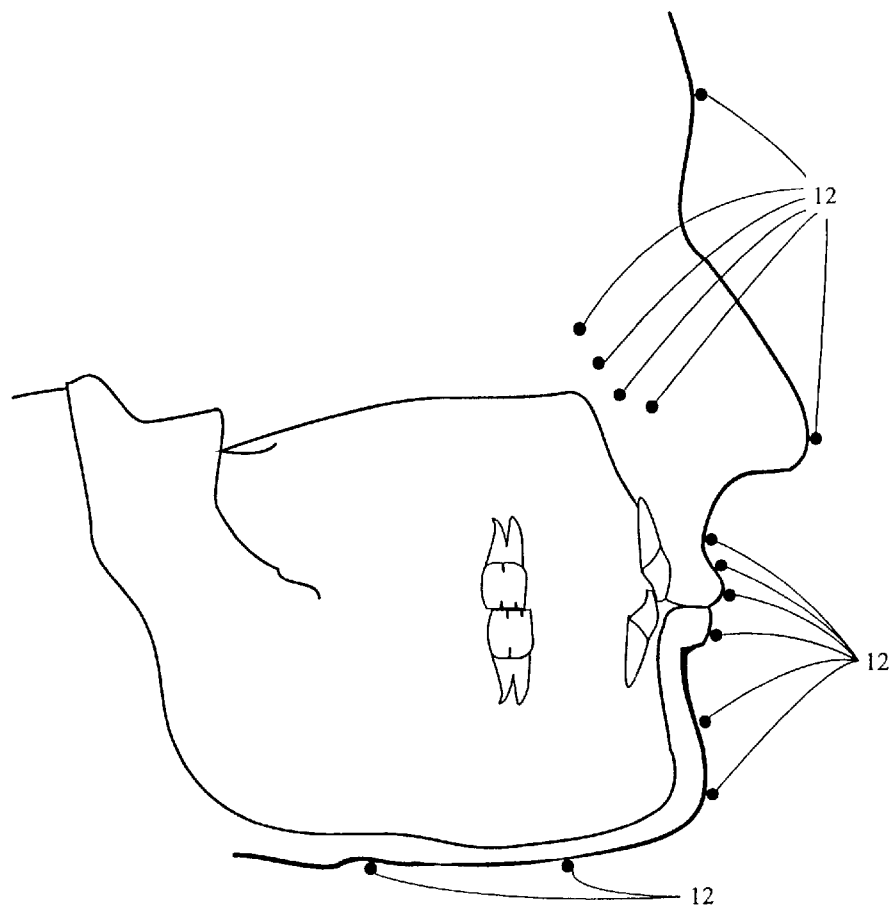
FIG. 7 is a diagrammatic profile view of an X-ray of patient's face with images of the radiopaque markers, and the facial profile shown.

Referring lastly to FIG. 7, a diagrammatic profile view of an X-ray of patient's face with images of spherical balls of radiopaque material of 12 radiopaque markers 10 or 30 clearly showing up and allowing extremely accurate measurement of soft tissue structures of the face (or for that matter any other part of the body) using traditional X-ray radiology. Again, since the images of the spherical balls of radiopaque material 12 and 38 will always be circular on the x-ray film regardless of the contours of the tissue to which they are applied and the angle of the X-ray machine to the body, extremely accurate, and easy to evaluate results can be gained.

The radiopaque markers 10 and 30 of the invention can be conveniently used in radiological imaging and soft tissue landmark identification in analyzing a patient's body, such as his or her face and head. A plurality of radiopaque markers 10 or 30 can be applied to desired soft tissue landmarks of the patient, such as along points of his or her profile, and on other soft tissue points not along a landscape, such as the anterior-most projection of the cheek, the lowermost portion of the orbital rim, and the alar base.

A simple X-ray image can then be taken. The spherical balls of radiopaque material 12 will clearly show up on the X-ray film as circles, independent of the contour of the body part to which the radiopaque markers 10 and 30 are applied. Using these soft-tissue landmarks, the medical professional can make important measurements and calculations and use of this data for corrective surgery or otherwise.

There are various software packages which permit an X-ray image to be scanned into a computer, digitized, and used for making various calculations which the health care professional can use in diagnosis and treatment. The inventors radiopaque markers 10 and 30 and method are ideally suited for use with various software products, or on a stand alone basis.

The drawings and the foregoing description are not intended to represent the only form of the invention in regard to the details of its methodology and manner of operation. In fact, it will be evident to one skilled in the art that modifications and variations may be made without departing from the spirit and scope of the invention. Although specific terms have been employed, they are intended in a generic and descriptive sense only and not for the purpose of limitation.

I claim:

1. A radiopaque marker for use in nuclear medicine imaging of a patient's skin, comprising:

a spherical ball of radiopaque material; and non-radiopaque adhesive means adapted for releasably retaining the spherical ball of radiopaque material so that a portion of the spherical ball of radiopaque material is adapted to be retained closely against a patient's skin.

2. The radiopaque marker of claim 1, wherein the adhesive means comprises a sheet of film with an adhesive layer, the sheet of film overlaying a portion of the spherical ball of radiopaque material and having exposed portions for releasable attachment to a patient's skin.

3. The radiopaque marker of claim 1, wherein a plurality of the radiopaque markers are carried on a sheet of release film.

4. The radiopaque marker of claim 2, wherein the radiopaque marker further comprises a non-adhesive grip portion.

5. The radiopaque marker of claim 4, wherein the non-adhesive portion comprises a pull-tab means on an edge of the sheet of film.

6. The radiopaque marker of claim 1, wherein the spherical ball of the radiopaque material ranges in size from one to four millimeters.

7. The radiopaque marker of claim 1, wherein the radiopaque marker is for use in X-ray radiology.

8. The radiopaque marker of claim 1, wherein the spherical ball of radiopaque material is retained in a non-radiopaque body portion with a grip portion.

9. A radiopaque marker for use in x-ray radiology for marking the position of soft tissue landmarks, comprising:

a spherical ball of radiopaque material;

a sheet of film with a lower, adhesive layer, wherein the spherical ball of radiopaque material is adhered to a portion of the adhesive layer leaving exposed portions of the adhesive layer and leaving portions of the spherical ball of radiopaque material available for placement against the patient's skin;

a non-adhesive pull-tab portion extending from an edge of the sheet of film; and a sheet of release film from which the sheet of film and spherical ball can be releasably removed.

10. The radiopaque marker of claim 9, wherein the spherical ball of radiopaque material ranges in size from one to four millimeters.

11. A method for marking the positions of soft-tissue surface landmarks in nuclear medicine imaging, comprising the steps of:

providing radiopaque markers comprising spherical balls of radiopaque material with adhesive means for attaching the spherical balls of radiopaque material to the surface of the patient's skin;

applying the radiopaque markers to the surface of desired landmarks of he patient's skin which are desired to be imaged; and imaging the skin with the attached radiopaque markers to create a radiological image of the skin with the radiological markers appearing as circles thereon independent of from which angle the images are taken.

12. The radiopaque marker of claim 11, wherein the method is used for X-ray radiology.

* * * * *